United States Patent
Tornambe et al.

(10) Patent No.: US 10,064,717 B2
(45) Date of Patent: Sep. 4, 2018

(54) RETINAL REPAIR DEVICE AND METHOD

(71) Applicant: Poway Retinal Technologies, LLC, Poway, CA (US)

(72) Inventors: Paul E. Tornambe, Poway, CA (US); R. Todd McKinney, Rancho Santa Fe, CA (US); Patrick J. Fitzgerald, Poway, CA (US); Jasper Benke, San Diego, CA (US); John A. Simpson, Carlsbad, CA (US)

(73) Assignee: POWAY RETINAL TECHNOLOGIES, LLC, Poway, CA (US)

( * ) Notice: Subject to any disclaimer, the term of this patent is extended or adjusted under 35 U.S.C. 154(b) by 875 days.

(21) Appl. No.: 14/069,004

(22) Filed: Oct. 31, 2013

(65) Prior Publication Data
US 2014/0180411 A1    Jun. 26, 2014

Related U.S. Application Data

(60) Provisional application No. 61/721,081, filed on Nov. 1, 2012.

(51) Int. Cl.
*A61F 2/14* (2006.01)
*A61F 9/007* (2006.01)

(52) U.S. Cl.
CPC ............ *A61F 2/14* (2013.01); *A61F 9/00727* (2013.01)

(58) Field of Classification Search
CPC .................................. A61F 9/00727
See application file for complete search history.

(56) References Cited

U.S. PATENT DOCUMENTS

| | | | |
|---|---|---|---|
| 4,299,227 A | 11/1981 | Lincoff | |
| 5,286,261 A | 2/1994 | Roizenblatt | |
| 5,433,701 A * | 7/1995 | Rubinstein | A61F 9/00781 604/28 |
| 6,117,170 A | 9/2000 | Batdorf, Sr. | |
| 7,008,396 B1 * | 3/2006 | Straub | A61F 9/00781 604/8 |
| 2002/0197298 A1 * | 12/2002 | Yaacobi | A61K 9/0051 424/425 |
| 2006/0167422 A1 | 7/2006 | Shahinpoor et al. | |
| 2009/0163773 A1 | 6/2009 | Lin | |
| 2009/0254023 A1 | 10/2009 | Akduman | |
| 2010/0305694 A1 * | 12/2010 | Lee | A61F 9/00727 623/6.63 |

FOREIGN PATENT DOCUMENTS

FR    2806293 A1    9/2001

OTHER PUBLICATIONS

International Search Report and Written Opinion for related PCT Application No. PCT/US2013/067842, dated Jan. 22, 2014, in 12 pages.
Extended European Search Report of European application No. 13850550.8 dated Jun. 7, 2016 in 6 pages.

* cited by examiner

*Primary Examiner* — Leslie Lopez
(74) *Attorney, Agent, or Firm* — Procopio, Cory, Hargreaves & Savitch, LLP

(57) ABSTRACT

A device which may be formed of suitable elastomeric, biocompatible material is configured to be wedged into Tenon's space between the orbital and scleral walls of the eye at the location of a retinal tear or break. When positioned, the device pushes the eye wall inward to close the tear, and fluid below the retinal wall resorbs.

17 Claims, 8 Drawing Sheets

RETINAL REPAIR DEVICE AND METHOD

RELATED APPLICATIONS

This application claims the benefit of U.S. provisional application Ser. No. 61/721,081, filed Nov. 1, 2012, titled "RETINAL REPAIR DEVICE AND METHOD," which is hereby incorporated by reference.

BACKGROUND

Field of the Invention

The present invention relates generally to repair devices and methods for retinal tears and detachments, and is particularly concerned with non-inflatable retinal repair devices.

Related Art

Retinal detachment or separation can occur spontaneously, or due to myopia, cataract surgery, certain eye diseases, and long term medical conditions such as diabetes. Detachment occurs when vitreous liquid leaks through a retinal opening or tear and accumulates under the retina. As liquid accumulates, the retina may separate from the underlying layer, the retinal pigment epithelium. Normally, surgery is used to repair retinal tears, holes and detachments. In this type of surgery, known as scleral buckling, a device is attached to buckle the sclera using scleral sutures, flaps, encircling bands, or the like. The surgery may also include draining subretinal or removing anterior chamber fluid. The operation may also be combined by removing the vitreous gel and replacing it with a type of balanced salt solution, known as vitrectomy. Surgical buckles as used in such surgeries can produce discomfort and blurred vision, and can also lead to infection. The recovery period from such surgery is typically several months.

U.S. Pat. No. 4,299,227 of Lincoff describes a device known as the Lincoff balloon and a method of using the device for correcting retinal detachment using an expandable member which does not have to be secured to the sclera by sutures. A balloon is inserted into Tenon's space through a small incision and positioned above the retinal tear. It is then expanded to form an indention or scleral depression in the eye at the tear. The expanded balloon is left in place until the retina has reattached.

SUMMARY

Embodiments described herein provide for a non-inflatable device designed to provide a temporary plombage adapted to exert pressure on the wall of the eye and produce an indentation or depression at a retinal tear location.

According to one embodiment, a device is inserted between the orbital wall and sclera of the eye, in Tenon's space, and positioned at a retinal tear or opening in order to apply pressure to indent the wall of the eye directly beneath the retinal tear. The device may be of various different shapes and may be of non-compliant material in one embodiment, or may alternatively be of compliant or deformable material. In one embodiment, the device may be a substantially solid member or a hollow member of predetermined shape having at least partially rounded outer surfaces, and may be of a soft and deformable elastomeric material. Suitable shapes for the device are football shape, top hat shape, airfoil shape, spherical shape, cylindrical shape, other rod-like shapes, barbell shape, and the like. The device is wedged in between the orbital bone and the surface of the eye at the location of a retinal tear and detachment, and pushes the eye wall inward to close the tear. The device is left in position for an extended time period while fluid beneath the retina resorbs.

The above devices are primarily intended for use in treating retinal detachments in an office setting. Once the device is properly positioned to produce an indent or depression at the appropriate location, the fluid beneath the retina resorbs using the eye's natural retinal epithelial pigment pump, and the retina reattaches. The retina may then be tacked down using a laser to keep it from re-detaching. Alternatively, retinocryopexy may be applied to the retinal defect prior to insertion of the device. The device may also be used in an operating room setting alone as a definitive procedure or during vitrectomy procedures with or without opening the conjunctiva to indent the wall of the eye in order to permit removal of vitreous gel at the vitreous base. This eliminates the need for a skilled surgical assistant scrub nurse to provide scleral depression and makes the operation safer. The device may be customized, trimmed, or shaped during the procedure to best conform to the individual patient's eye, orbit and pathology.

The non-inflatable retinal repair devices described above do not require inflation after placement, and can remain in position for three or more days before being removed in the office. An adhesion around the tear is created either with cryopexy immediately before the device is inserted or with laser photocoagulation after the device is inserted.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a non-inflatable retinal repair device configured for placement or insertion into the periocular space between the sclera and the conjunctiva, Tenon's capsule, and/or the orbital wall at or adjacent a retinal tear location, so as to produce a temporary depression or indentation of the eye wall on the sclera over the break.

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 1:
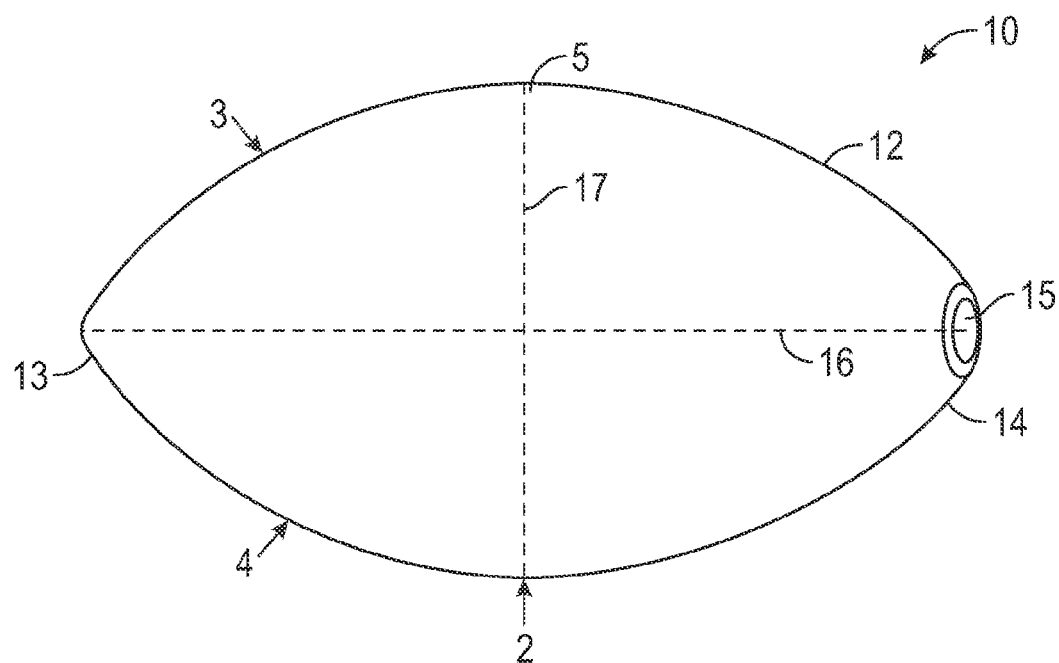
FIG. 1 is a perspective view of a first embodiment of a generally football shaped retinal repair device, on an enlarged scale.
Figure 2:
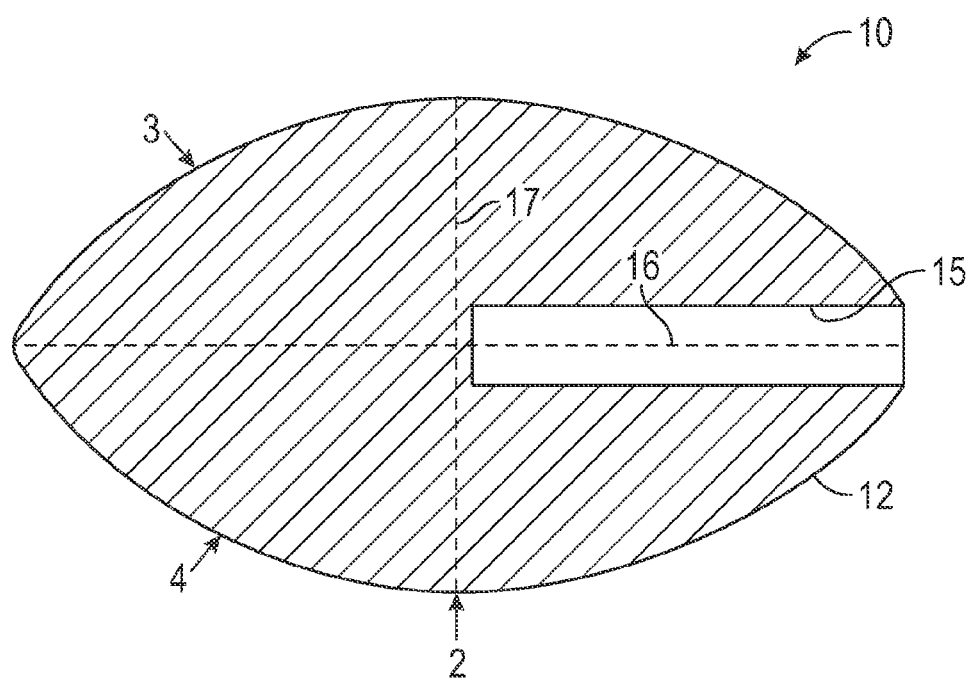
FIG. 2 is cross-sectional view of the device of FIG. 1, on a smaller scale than FIG. 1.

FIGS. 1 and 2 illustrate a first embodiment of a retinal repair device 10 comprising a member 12 including a posterior end 13 and an anterior end 14 opposite and distal to the posterior end 13. The member 12 may include an orbital facing surface 3 and a sclera facing surface 4, opposite the orbital facing surface 3. The member 12 may include a thickened portion 5 or a portion that is thickened to indent the sclera of an eye when the retina repair device is inserted into the periocular space, for example between the sclera and the orbital wall of the eye. The orbital facing surface 3 may be configured to contact the orbital wall of an eye. The thickened portion 5 may include a sclera contacting surface 2 that contacts and indents the sclera.

In the embodiment in FIGS. 1 and 2, the retinal repair device 10 may be a football-shaped or in the shape of a prolate spheroid. The orbital facing surface 3 and the sclera facing surface 4 may form the prolate spheroid shape. The thickened portion 5 may be formed by the prolate spheroidal shape at a minor axis 17 of the prolate spheroidal shape, and the sclera contacting surface 2 may be a portion of the sclera facing surface 4. The posterior end 13 and the anterior end 14 may be tapered and may be rounded or truncated, and are located at opposite ends of the major longitudinal axis 16 of the member 12.

As illustrated, the retinal repair device 10 may include bore 15 extending inwardly from anterior end 14 along the major longitudinal axis 16. Bore 15 may be a blind bore penetrating along the major longitudinal axis 16. In one embodiment, bore 15 penetrates to a depth of about 30 to 90 percent of its overall length, and in one embodiment the bore 15 penetrates to a depth of around 60 to 80 percent of the length of the major axis. In the embodiment shown in FIG. 2, bore 15 penetrates to a depth of 40 to 50 percent of the length of the major axis. Bore 15 is designed to receive the tip of a suitable delivery device 18 for positioning device 10 in the eye, as described in more detail below in connection with FIG. 3. Bore 15 may be a through bore in alternative embodiments, preferably accompanied by an additional hilt-like feature on the delivery device to control its insertion depth within the bore 15.

In some embodiments, retinal repair device 10 is formed of a soft and deformable material so that it deforms easily during insertion into the periocular space. The material may be selected from a variety of possible elastomers (elastic polymers) including silicone rubbers, urethanes, Pebaxes, Santoprenes, thermoplastic rubbers (TPR), or the like. The key criteria are low durometer (at or below approximately Shore 55D) for easy deformability, and biocompatibility. A thermoplastic elastomeric material is preferred over a thermoset due to simpler processability (thermoplastics are rapidly injection moldable by conventional means, whereas thermosets are generally not). In one embodiment, a Pebax® elastomer or block copolymer supplied by Arkema Inc. of King of Prussia, Pa. may be used as the material for the retinal repair device. Pebax® elastomers are biocompatible and the ratio of its homopolymer constituents can be varied to produce a wide variety of durometer levels. In one example, Pebax 3533 SA01 was used as the material for device 10. This material has a durometer of Shore 35D and is a thermoplastic with good injection molding characteristics. The device 10 may be made of absorbable material, or of such material which acts as a reservoir for drugs, stem cells, viral vectors, or neurotrophic agents.

The major longitudinal axis 16 of member 12 may have a length in the range from 15 mm to 25 mm and the minor axis 17 may have a length or diameter in the range from 8 mm to 12 mm, defining the thickness of device 10. In one embodiment, a series of three devices 10 of gradually increasing thicknesses at the minor axis may be used. In one embodiment, these thicknesses are 8 mm, 10 mm and 12 mm. These devices 10 may be used to apply gradually more force over time and produce successively greater indentation in the area of a retinal tear or opening, as discussed in more detail below.

Figure 3:
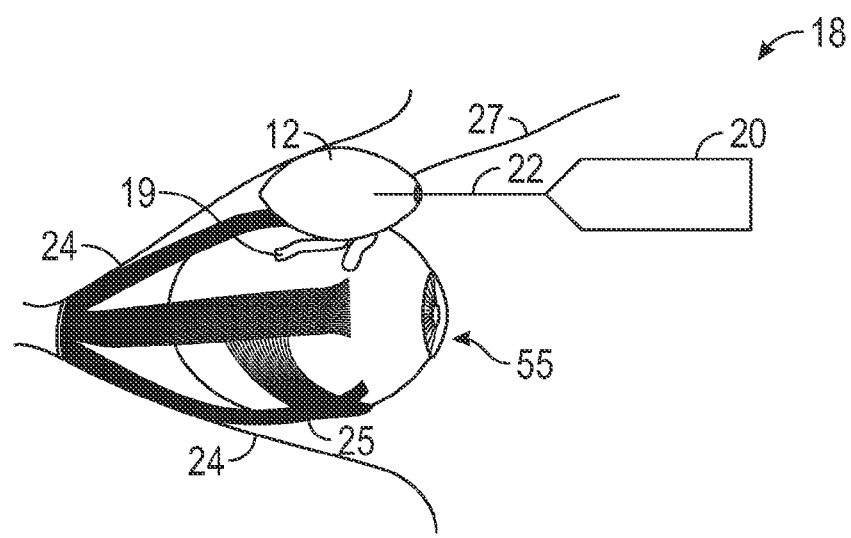
FIG. 3 is side view showing the device of FIGS. 1 and 2 mounted on a delivery or insertion device as the device is placed in the final insertion position between the orbital wall and sclera of the eye, at a selected location corresponding to a retinal tear.
Figure 4:
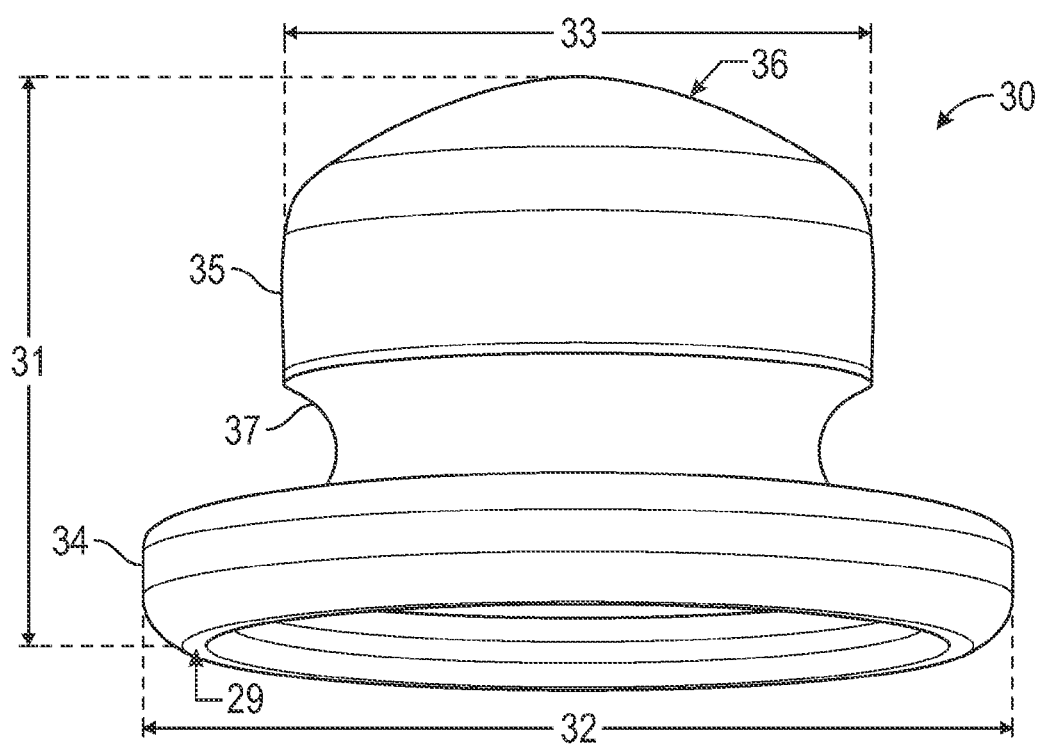
FIG. 4 is a front elevation view of a second embodiment of a retinal repair device, on an enlarged scale.
Figure 5:
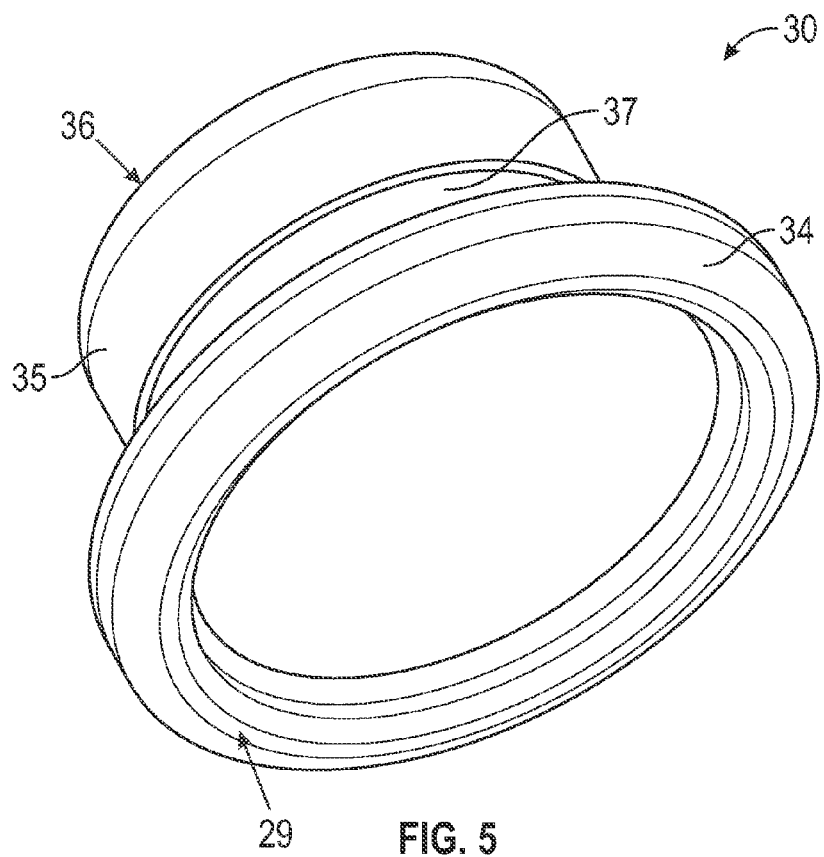
FIG. 5 is a bottom elevation view of the device of FIG. 4.
Figure 6:
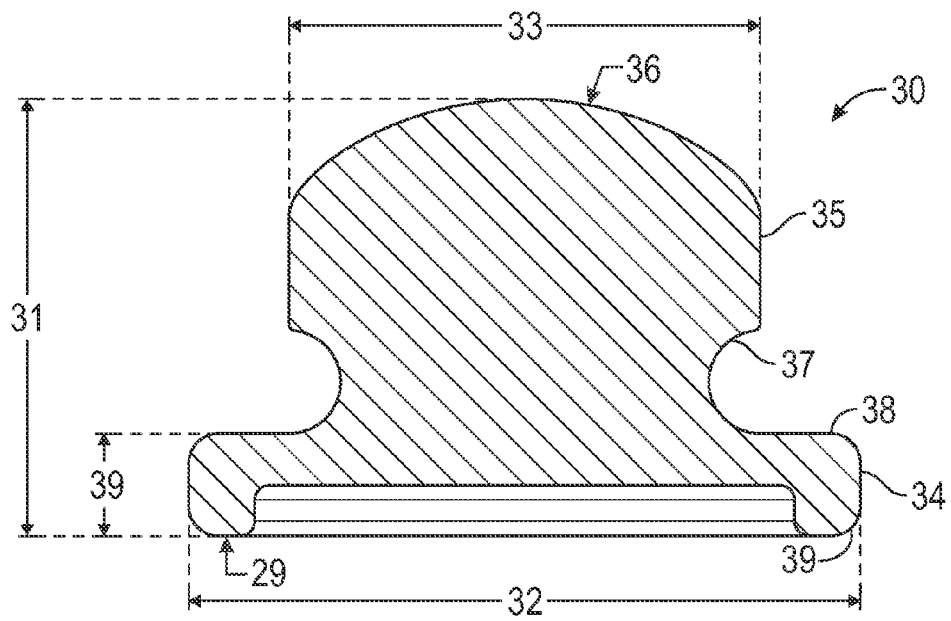
FIG. 6 is a cross-sectional view of the device of FIGS. 4 and 5.

FIG. 3 shows the device 10 of FIGS. 1 and 2 mounted on a delivery or insertion device 18 as the retinal repair device 10 is placed in the final insertion position in the periocular space, such as between the orbital wall 24 and the sclera 25 of the eye 55 at a selected location corresponding to a retinal tear 19. As illustrated in FIG. 3, a suitable delivery device 18 such as a surgical probe or blunt hypodermic needle may be used for positioning retinal repair device 10 at the appropriate location between the orbital wall 24 and sclera 25. Delivery device 18 has a handle 20 and a probe or needle 22 projecting from the handle 20, shown engaged in the bore 15. The diameter of bore 15 is similar to that of probe or needle 22. Device 10 is wedged between the bony orbit or orbital wall 24 and the eye wall or sclera 25 of the eye 55, after making a small incision in the conjunctiva in the desired meridian of a retinal tear 19. The tapered posterior end 13 of member 12 makes insertion easier, and the soft, deformable material of member 12 further eases insertion. Once device 10 is properly positioned over a tear or opening 19 in the retina, as illustrated in FIG. 3, delivery device 18 is withdrawn.

Once wedged in position, the football device pushes the eye wall inward to close the tear, as indicated in FIG. 3. The rounded outer surface of member 12 provides a temporary 'plombage' or 'push' which indents the wall of the eye 55, directly everlying a retinal break(s) which is responsible for the retinal detachment. As the eye 55 softens under this pressure, the sclera is pushed towards the retinal break, and eventually closes the retinal break by pushing, pressing, or opposing the retinal pigment epithelium against the detached sensory retina. In doing so the fluid beneath the retina resorbs using the eye's natural retinal pigment epithelial 'pump' and the retina attaches. When the fluid resorbs (usually in a day or less) because the retinal defect is closed, and the body pumps the fluid out naturally from beneath the retina, a laser can be applied to tack down the retina and prevent it from re-detaching. The retina must be attached before the laser is applied. Once the laser is applied, the device remains in place for several more days giving the laser marks time to form an adhesion, and can then be removed in the doctor's office. If we think of the laser as glue, it takes a few days for it to set. As illustrated in FIG. 3, a tether 27 may be attached to member 12 to allow for removal after sufficient time has elapsed for adhesion. Tether 27 may be constructed of Dacron® or other medical grade material.

As noted above, device 10 may be provided in a series of progressively increasing diameters, lengths, or thicknesses for minor axis 17. In one embodiment, the smallest diameter device (8 mm) is first inserted in the desired position, as in FIG. 3, and left in place for a selected time period so as to indent the wall of the eye 55 by a first amount. The smallest diameter device is then removed and replaced with the intermediate diameter device (10 mm) which is left in place so as to increase the size of the indent, and then replaced with the largest diameter device (12 mm). This avoids or reduces the risk of possible trauma as a result of installing a device of relatively large diameter first, and instead allows the size of the indent to be progressively increased. Device 10 may be provided in different amounts of gradually increasing diameters or thicknesses in alternative embodiments, depending on the type of trauma and amount of push or indentation required.

FIGS. 4 to 7 illustrate a retinal repair device 30 according to a second embodiment. In this embodiment, device 30 comprises a one piece molded member of a generally "top hat" shape, having an annular rim 34 and a cylindrical or thickened portion 35. Annular rim 34 may be a hollow cylinder with a closed end and an open end. The closed end is the end adjacent thickened portion 35. Annular rim 34 may include an orbital facing surface 29 at the open end. Orbital facing surface 29 may be configured to contact the orbital wall of an eye. The edges 38 and 39 of annular rim 34 may be rounded.

Thickened portion 35 is cylinder of solid cross-section extending axially from annular rim 34. Thickened portion 35 includes an end face or a sclera facing surface 36 distal to the annular rim 34 and the orbital facing surface 29. Sclera facing surface 36 may be outwardly rounded or part spherical, such as a spherical cap. At least a portion of sclera facing surface 36 may be a sclera contacting surface configured to contact and indent the sclera of an eye. Thickened portion 35 may also include a neck 37. Neck 37 may be an undercut or recess located at the intersection of thickened portion 35 and annular rim 34, adjacent the annular rim 34, extending around the perimeter or circumference of the thickened portion 35. Device 30 may be formed of materials similar or identical to those described above in connection with the first embodiment. As illustrated, the width 33 of thickened portion 35 is smaller than the width 32 of annular rim 34. The height 31 of the device 10 is around 6.5 mm, the width 33 of the thickened portion 35 is around 7.0 mm, and the width 32 of annular rim 34 is around 10.0 mm. Edges 38 and 39 may be rounds around 0.5 mm.

Figure 7:
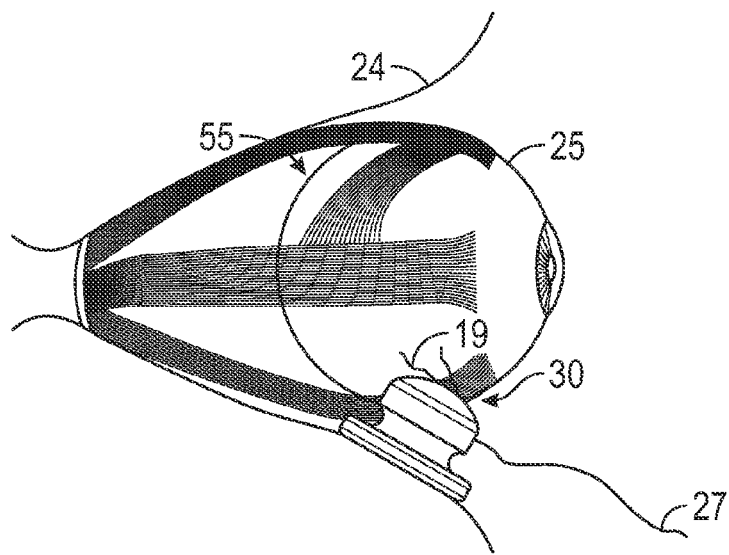
FIG. 7 is a side view illustrating the device of FIGS. 4 to 6 positioned in the space between the orbital wall and sclera of the eye and bearing against a part of the sclera including a retinal tear.
Figure 8:
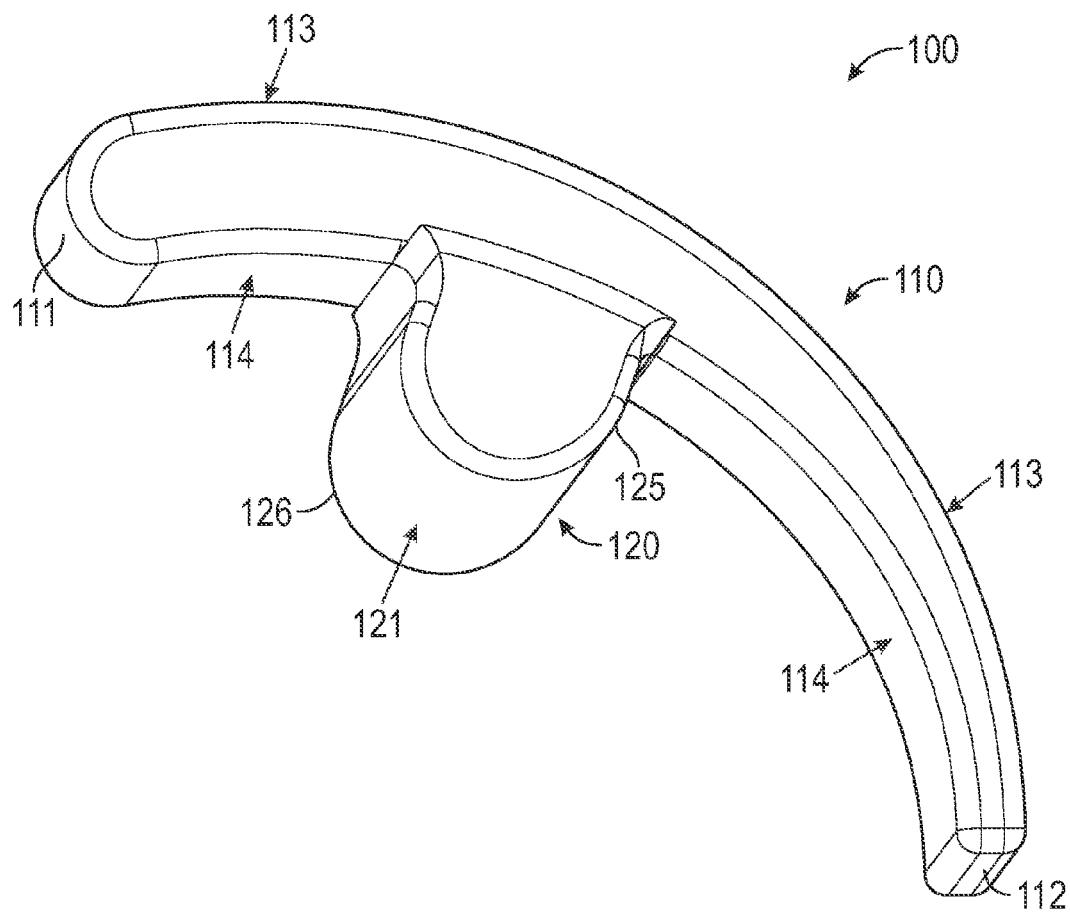
FIG. 8 is a perspective view of a third embodiment of an airfoil shaped retinal repair device, on an enlarged scale.
Figure 9:
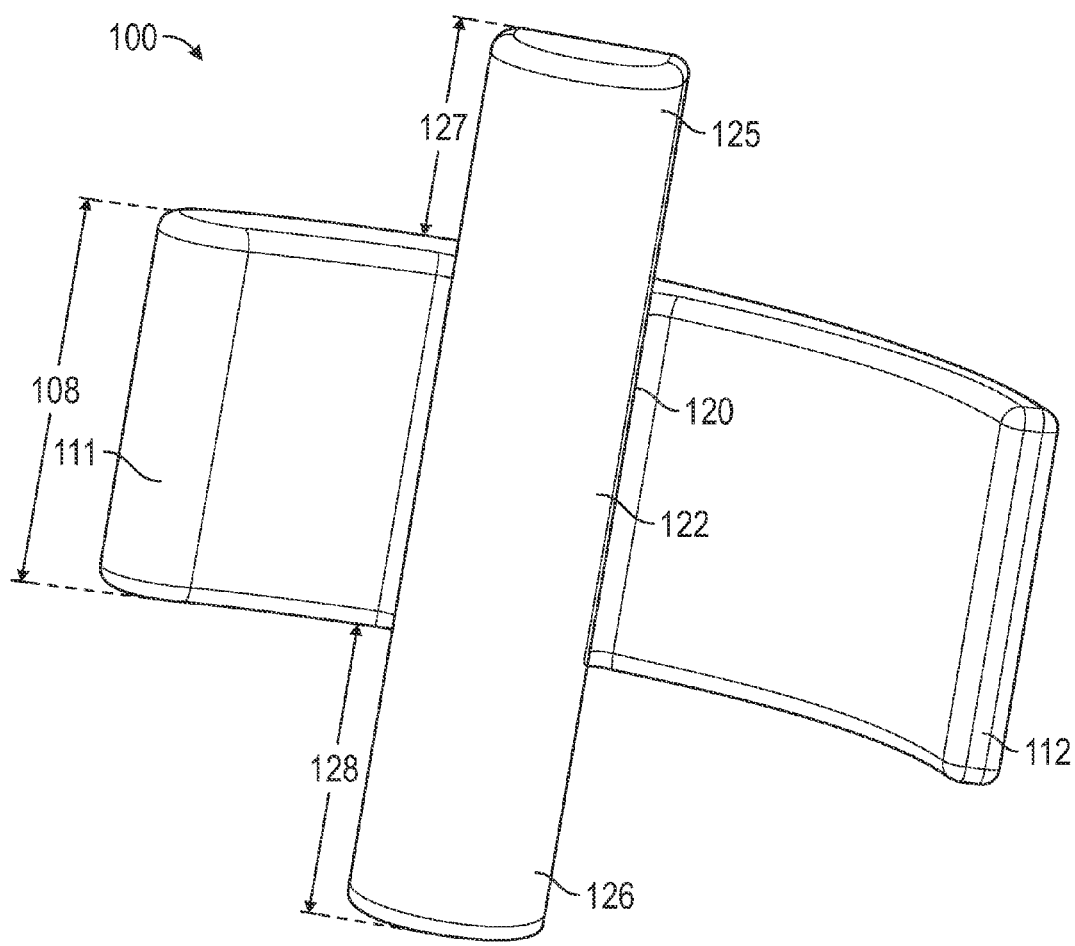
FIG. 9 is a bottom elevation view illustrating the device of FIG. 8.
Figure 10:
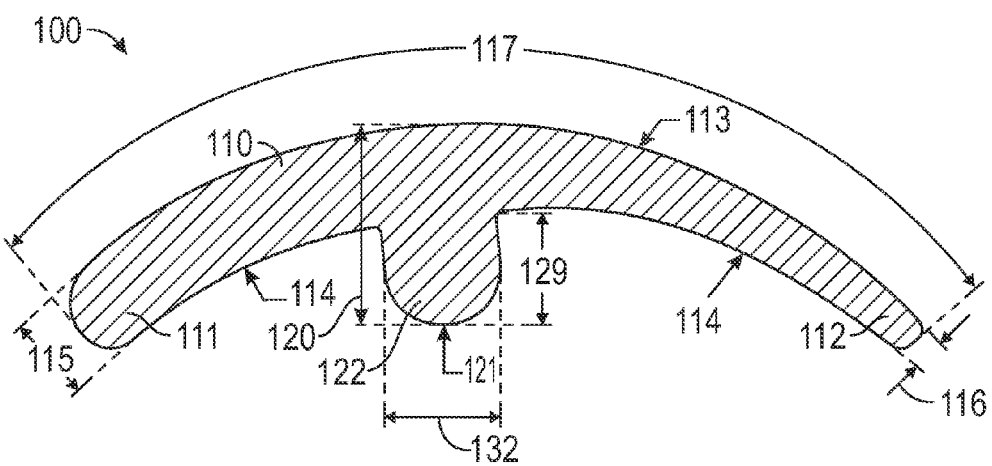
FIG. 10 is a cross-sectional view of the device of FIGS. 8 and 9.
Figure 11:
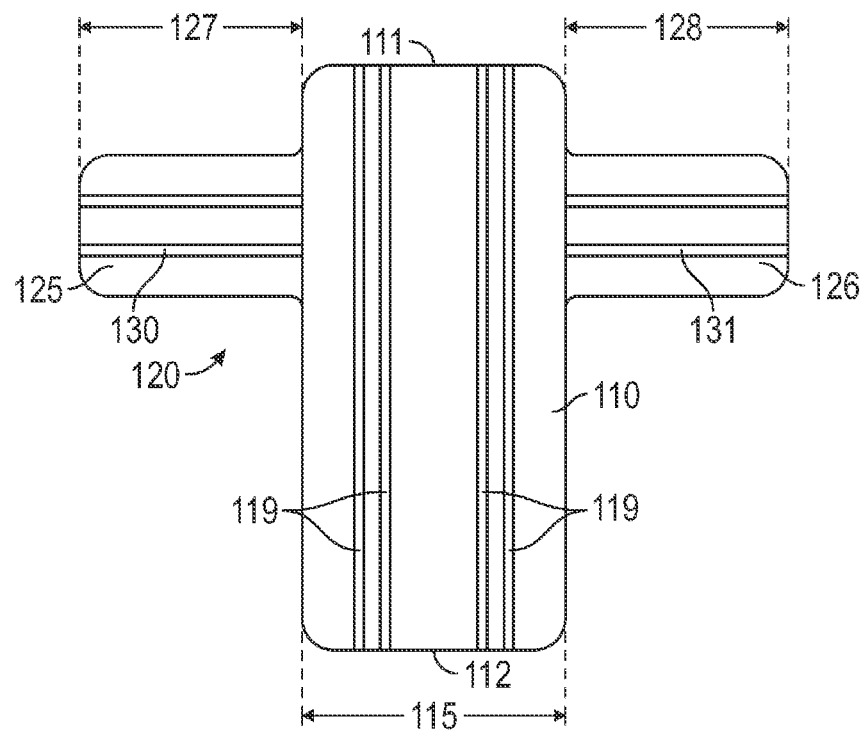
FIG. 11 is a top view of the device of FIGS. 8 to 10.
Figure 12:
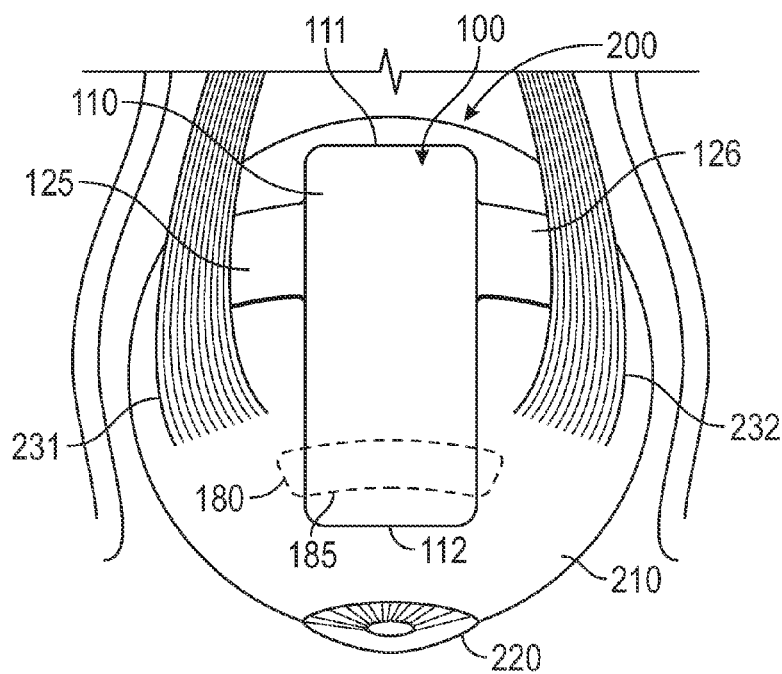
FIG. 12 is a perspective view of the device of FIGS. 8 to 11 positioned against the sclera of the eye and bearing against a part of the sclera including a retinal tear.

FIG. 7 illustrates the device 30 positioned between the orbital wall 24 and sclera 25 of the eye 55 over a retinal tear 19, with the annular rim 34 bearing against orbital wall 24 and the sclera facing surface 36 of thickened portion 35 bearing against the location of the retinal tear 19. Neck 37 may be included to enable the device 30 to be gripped by a tweezers with appropriately curved tips or similar device for insertion and retrieval. Device 30 may also or alternatively include a bore for engaging a delivery device and a tether 27 as illustrated for the embodiment of FIGS. 1 to 3. As in the previous embodiment, a series of top hat shaped devices of progressively increasing height 31 may be provided, for progressively increasing the size of the indentation at a retinal tear or the like.

FIGS. 8 to 12 illustrate a retinal repair device 100 according to a third embodiment. In this embodiment, device 100 includes an elongated portion 110 and a thickened portion 120. Elongated portion 110 includes a posterior end 111, an anterior end 112, an orbital facing surface 113, and a sclera facing surface 114, located opposite the orbital facing surface 113. In embodiments, the sclera facing surface 114 is radially inward from the orbital facing surface 113. Posterior end 111 and anterior end 112 may each include a round, the round being rounded edges or a rounded surface. Anterior end 112 is distal to posterior end 111. Orbital facing surface 113 and sclera facing surface 114 may each extend from posterior end 111 to anterior end 112. The profiles of orbital facing surface 113 and sclera facing surface 114 may be curved and may be circular, elliptical, and the like. In the embodiment illustrated in FIGS. 8 to 12, the centers of curvature for orbital facing surface 113 and sclera facing surface 114 are on the same side of elongated portion 110.

In the embodiment illustrated, orbital facing surface 113 and sclera facing surface 114 are not concentric forming a wedge or airfoil shape. Posterior end 111 is thicker than anterior end 112. Elongated portion 110 gradually gets thinner from posterior end 111 to anterior end 112 with the sclera facing surface 114 converging towards the orbital facing surface 113 from posterior end 111 to anterior end 112. The profile of elongated portion 110 may be the shape of a portion of a crescent, a lune, or a meniscus lens located within half of the crescent, the lune, or the meniscus lens with rounded ends or edges.

Thickened portion 120 may include a protrusion 122 extending or protruding inward from elongated portion 110. The protrusion 122 may extend from sclera facing surface 114 in the direction opposite orbital facing surface 113. The protrusion 122 may form a ridge extending across a portion or the entire width 108 of elongated portion 110, the width being transverse to the profile of elongated portion 110. The protrusion 122 may extend perpendicular to sclera facing surface 114.

Thickened portion 120 includes sclera contacting surface 121. Sclera contacting surface 121 may also include a round and is configured to contact the sclera 210 of the eye 200 at the location of the retinal break or tear. In the embodiment illustrated in FIGS. 8-12, sclera contacting surface 121 is located at the end of the protrusion 122 distal to the orbital facing surface 113 and the sclera facing surface 114.

Device 100 may also include wings projecting beyond the width 108 of elongated portion 110. The wings may extend from the thickened portion 120 including the protrusion 122 or elongated portion 110, lateral to elongated portion 110. In the embodiment illustrated, device 100 includes a first wing 125 and a second wing 126. First wing 125 and second wing 126 project from the protrusion 122 of thickened portion 120 in opposite directions, both being transverse or lateral to the profile of elongated portion 110. First wing 125 and second wing 126 may have the same or a similar shape to the shape of the protrusion 122. In this embodiment, the profiles of the protrusion 122, first wing 125 and second wing 126 are each an extruded half round, a semi-circle with an adjacent rectangle extending from the semi-circle with the width of the rectangle equaling the diameter of the semi-circle. Other shapes and configurations for the wings may also be used.

Protrusion 122, and the wings, such as first wing 125 and second wing 126 may form a cross-member. In some embodiments, this cross-member may be adjustable in its location up and down the sclera facing surface 114 of elongated portion 110. The cross-member and elongated portion 110 may be separate parts of different sizes, and may be different materials, which can be fixed together, used separately, or mixed and matched as needed for each situation.

The edges, ridges, and corners of device 100 may be rounded. All or some of the surfaces of device 100 including orbital facing surface 113, sclera facing surface 114 and sclera contacting surface may include surface features such as dimples or pads for gripping purposes, and may have coatings of materials or layers of woven materials such as Dacron® or other medical grade materials adhered to the surface or surfaces to aide in gripping tissue and preventing migration of the device after implant. Tissue glues and sutures may also be used to fix the device in place after implant.

The posterior (distal) thickness 115 of the posterior end 111 may be from 4 mm to 10 mm. In the embodiment illustrated, the posterior thickness 115 is 4 mm or approximately 4 mm and the anterior (proximal) thickness 116 of anterior end 112 is 2 mm or approximately 2 mm. The length 117 of device 100, from posterior end 111 to anterior end 112, may be from 18 mm to 25 mm. Length 117 may be an arc length. Width 108 of elongated portion 110 may be from 6 mm to 10 mm. The ridge height 129 of the protrusion 122, the distance from sclera facing surface 114 to sclera contacting surface 121, may be from 6 mm to 12 mm. The ridge width 132 of protrusion 122 may be from 5 mm to 10 mm. The first wing length 127, the distance first wing 125 extends beyond the edge of elongated portion 110, and the second wing length 128, the distance second wing 126 extends beyond the edge of elongated portion 110, may be from 4 mm to 8 mm.

In the embodiment illustrated, the length of the protrusion 122 extending across width 108 is equal to width 108. In other embodiments, such as some of the embodiments without wings, the length of the protrusion 122 extending across width 108 may be from 4 mm to 8 mm.

Device 100 may be formed of materials similar or identical to those described above in connection with the first embodiment and the second embodiment, or may be of firmer durometer materials. The curvature of elongated portion 110 is designed to generally follow the external contour of the eye. In some embodiments, the radius of curvature is from 10 mm to 14 mm. In other embodiments, such as the embodiment illustrated in FIG. 11, device 100 includes one or more bendable rods 119, 130, and 131. Elongated portion 110 may include one or more bendable rods 119, first wing 125 may include one or more bendable rods 130, and second wing 126 may include one or more bendable rods 131. In the embodiment illustrated, bendable rods 119 traverse orbital facing surface 113 from posterior end 111 to anterior end 112. In other embodiments, bendable rods 119 may be embedded in elongated portion 110 and may traverse all or part of elongated portion 110. Similarly, bendable rods 130 and 131 may traverse all or a portion of first wing 125 and second wing 126 respectively, extending in the same direction as first wing 125 and second wing 126, perpendicular to bendable rods 119. Bendable rods 130 and 131 may extend along the outer surfaces or be embedded in first wing 125 and second wing 126. Bendable rods 119, 130, and 131 may be a malleable metal or similar material that allows for the modifying and customization of a radius of curvature of the elongated portion 110, the first wing 125, and the second wing 162 by bending the bendable rods 119, 130, and 131 respectively.

The protrusion 122 is configured to provide the necessary focal pressure to the eye 200 to indent the sclera over the area of the retinal tear. Device 100 may be controlled and inserted into the periocular space with a small grasper. The sclera contacting surface 121 of device 100 is configured to contact the sclera 210 with the orbital facing surface 113 is configured to contact the orbital wall (not shown). First wing 125 and second wing 126 are positioned under muscles 231 and 232 respectively to stabilize and anchor device 100 to prevent migration. Device 100 may further be stabilized and held in the desired position by wedging the anterior (proximal or limbal) end 112 closest to the cornea 220 under the conjunctiva flap or pocket created near the limbus (not shown). Incised edges of the conjunctiva can then be sutured together to effectively trap device 100 in position and prevent device 100 from being extruded or pushed out of position.

The device 100 may be sutured directly to the sclera using absorbable or non-absorbable suture material. The device 100 itself may be made of absorbable material. In the embodiment illustrated in FIG. 12, device 100 includes suture holes 185. Suture holes 185 may be located proximal to the anterior end 112. Suture 180 may be used to further stabilize device 100 by suturing device 100 to the sclera 210 through suture holes 185.

While device 100 in the embodiment illustrated in FIGS. 8 to 12 show elongated portion 110 with a curved profile, in other similar embodiments, elongated portion 110 may be initially formed in a straight wedge shape with orbital facing surface 113 converging towards sclera facing surface 114 from posterior end 111 to anterior end 112. The elongated portion 110 can then be bent or formed into the curved shape prior to installation to match the curvature of the eye 200. The bendable rods 119 may help elongated portion 110 maintain the curved shape. Similarly, first wing 125 and second wing 126 may be initially formed as straight extensions from the elongated portion 110. First wing 125 and second wing 126 can then be bent or formed into curved shapes prior to installation to match the curvature of the eye 200. The bendable rods 130 and 131 may help the first wing 125 and the second wing 126 maintain the curved shapes.

Figure 13:
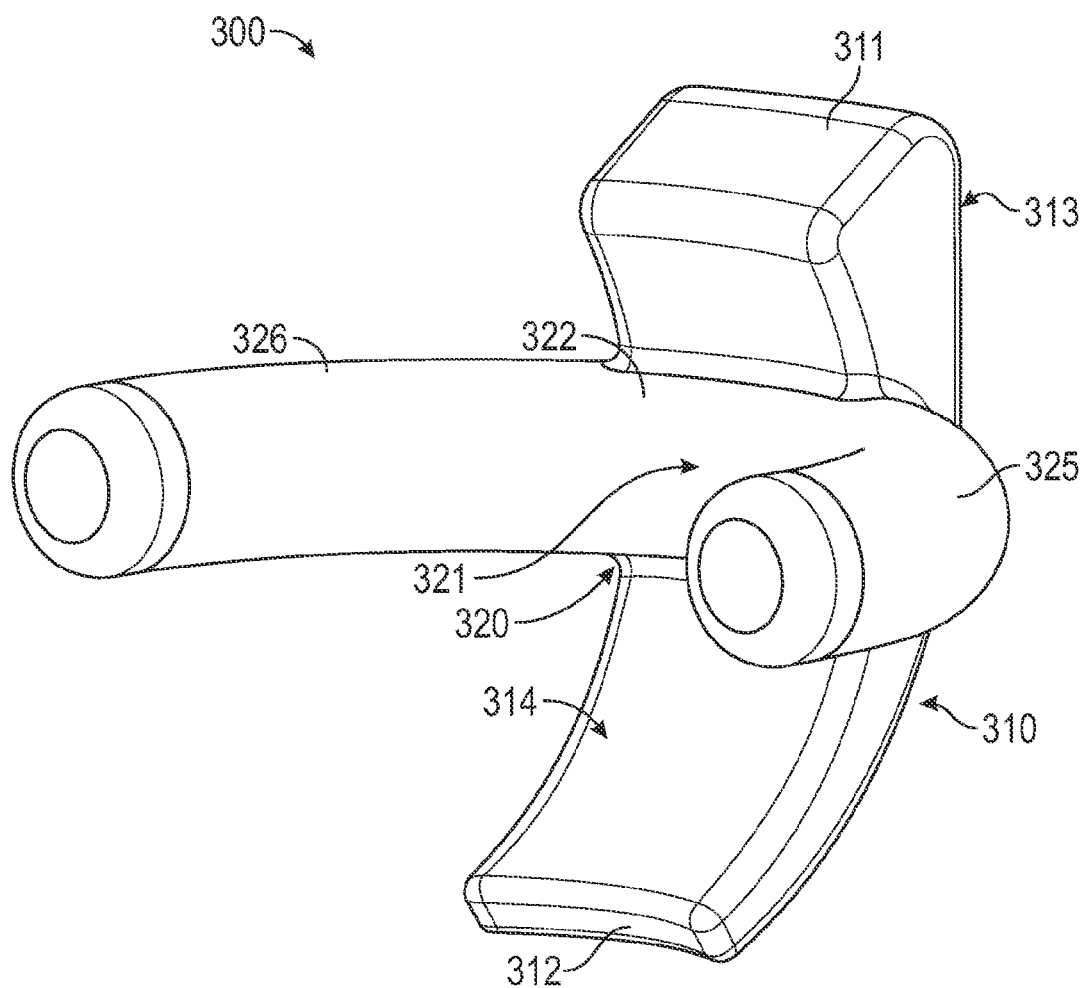
FIG. 13 is a perspective view of a fourth embodiment of a retinal repair device, on an enlarged scale.

FIG. 13 illustrates a retinal repair device 300 according to a fourth embodiment. In this embodiment, device 300 includes an elongated portion 310 and a thickened portion 320 similar to those of device 100. The shapes lengths, widths, dimensions, and features of device 300 may be the same or similar to those of device 100. Elongated portion 310 also includes a posterior end 311, an anterior end 312, an orbital facing surface 313, and a sclera facing surface 314, located opposite the orbital facing surface 313. In the embodiment illustrated in FIG. 13, posterior end 311 includes a flat surface with rounded edges between posterior end 311 and orbital facing surface 313, and posterior end 311 and sclera facing surface 314.

In the embodiment illustrated in FIG. 13, thickened portion 320 includes protrusion 322 extending from sclera facing surface 314 and is cylindrically shaped, such as a half cylinder. Device 300 includes a first wing 325 and a second wing 326 extending from elongated portion 310 and protrusion 322 in opposite directions. First wing 325 and second wing 326 each include a cylindrical shape that is curved. The curvature of elongated portion 310, the first wing 325, and the second wing 326 may be configured to match or approximate the curvature of the eye. The sclera contacting surface 321 of protrusion 322 may also be configured to match the curvature of the eye in the direction that protrusion 322 extends. Device 300 may also include bendable rods for reshaping the curves of elongated portion 310, first wing 325, and second wing 326.

Figure 14:
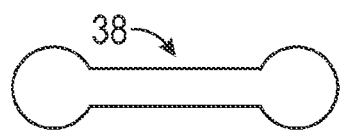
FIGS. 14 to 19 illustrate some possible alternative shapes for the retinal repair device.
Figure 15:
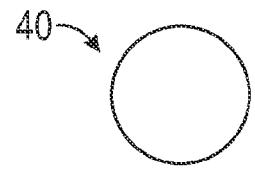

FIGS. 14 to 19 illustrate some possible alternative shapes for a retinal repair device of deformable material as described above. FIG. 14 illustrates a retinal repair device 38 of dumbbell shape, while the device 40 of FIG. 15 is spherical. Device 38 may have a length in the range from 8 mm to 12 mm, with one end of the device designed to bear against the orbital wall and the opposite end bearing against the sclera to form an indent. This device, with or without wings, may be useful for more posterior retinal tears requiring a more posterior plombage. The diameter of spherical device 40 may also be in the range from 8 mm to 12 mm.

Figure 16:
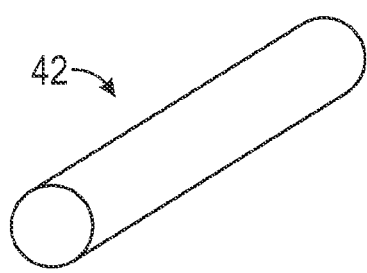
Figure 17:
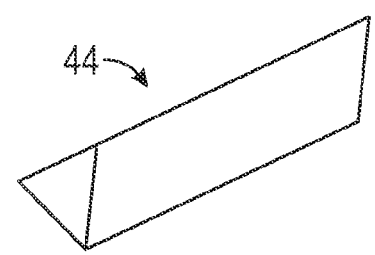
Figure 18:
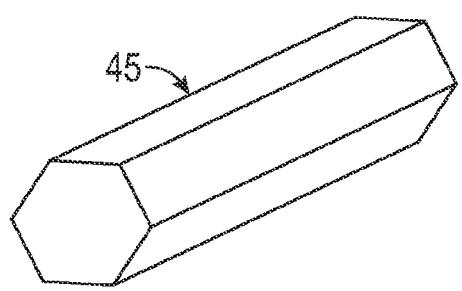
Figure 19:
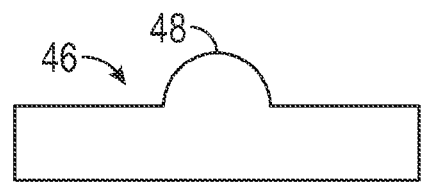

FIGS. 16 to 19 illustrate various rod-shaped devices, with FIG. 16 illustrating a cylindrical rod 42, FIG. 17 illustrating a rod 44 of triangular cross-section, FIG. 18 illustrating a rod 45 of hexagonal cross-section, and FIG. 19 illustrating a rectangular rod 46 with a thickened portion, bump, or protrusion 48 at an intermediate position in its length designed for bearing against the location of a retinal tear when suitably positioned in the eye, similar to the embodiment illustrated in FIGS. 8 to 12. The rectangular rod 46 has a cuboid shape rather than a wedge shape and may include the same or similar features ends, and surfaces as those described in conjunction with the third embodiment, including the orbital facing surface, the sclera facing surface, and the sclera contacting surface. These devices also may include a tether for removal purposes, as illustrated in FIG. 3 for the first embodiment, as well as blind bores for engagement with delivery devices. The rod-like devices are inserted lengthwise, i.e. with a middle region of the rod engaging the orbital wall and bearing against the sclera or wall of the eye at the location of a retinal tear.

In some embodiments, the devices of FIGS. 16 to 19 may have lengths in the range from 15 mm to 25 mm, and the devices in FIGS. 14 to 18 may have diameters in the range from 8 mm to 12 mm. The device of FIG. 19 may have a thickness at the bump in a similar range.

The retinal repair devices of FIGS. 1 to 19 may all be made of deformable elastomeric materials as described above in connection with the first embodiment. Although the devices above are of generally solid cross-section, apart from bores for receiving the shaft or probe of an insertion tool, in other embodiments one or more inflatable reservoirs may be provided for real-time adjustment of shape or size. In other embodiments, any of the devices described above and illustrated in FIGS. 1 to 19 may be of non-deformable material. The devices may also be made of materials which are hydroscopic, i.e. which swell or expand with absorption of moisture.

The materials of any of the devices described above may be non-resorbable or resorbable, and may include drug-eluting means such as reservoirs communicating with holes in the surface of the device. The reservoirs may also be used for stem cells, viral vectors, or neurotrophic agents. The devices may have surface features such as dimples or pads for gripping purposes, and may have coatings of materials or layers of woven materials such as Dacron® or other medical grade materials. The coatings or layers of woven materials may provide traction with surrounding tissue to help the devices disclosed above resist migration. Additionally, the devices may include embedded radioopaque markers for location and positioning of the devices through fluoroscopy or other imaging modalities. The devices may also include compartments for containing materials for use in radiotherapy or chemotherapy for treatment of ocular cancers, vascular diseases including venous and arterial occlusions, macular degeneration, glaucoma, or ocular inflammations.

The devices described above may remain in position for 3 or more days and then may be removed in the doctor's office. A string or suture may be attached to the device to indicate its presence and/or to aid in its removal, as illustrated in connection with the first embodiment. An adhesion around the tear can be created either with cryopexy immediately before the device is inserted or using laser photocoagulation after the device is inserted. Some cases may require both cryopexy and laser treatments.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art.

We claim:

1. A retinal repair device for insertion into a periocular space adjacent a retinal tear in an eye, the retinal repair device comprising:
   an elongated portion, a first wing portion and a second wing portion, the elongated portion having a central longitudinal axis and being of solid cross-section along the central longitudinal axis;
   the elongated portion including:
      a posterior end,
      an anterior end, opposite the posterior end,
      first and second opposite sides,
      an orbital facing surface extending from the posterior end to the anterior end,
      a sclera facing surface which is pre-formed prior to insertion of the device into the periocular space to have a concave curvature extending from the posterior end to the anterior end, opposite the orbital facing surface and configured to face a scleral surface of the eye with at least part of the sclera facing surface contacting the scleral surface; and
   a wing member comprising the first and second wing portions, a portion of the wing member between the first and second wing portions in contact with and extending from the scleral facing surface of the elongated portion, and
   the first wing portion and the second wing portion extending outwardly in opposite directions transverse to the longitudinal axis of the elongated portion and beyond the first and the second opposite sides, respectively, and each wing portion is spaced in its entirety from the posterior and the anterior ends.

2. The retinal repair device of claim 1, wherein the orbital facing surface and the sclera facing surface are curved with the orbital facing surface being convex and the sclera facing surface being concave, and wherein the elongated portion has a protrusion projecting from the sclera facing surface in a direction opposite the orbital facing surface, an end of the protrusion including the sclera contacting surface.

3. The retinal repair device of claim 2, wherein the posterior end is thicker than the anterior end, and the sclera facing surface converges towards the orbital facing surface from the posterior end to the anterior end.

4. The retinal repair device of claim 1, wherein the posterior end is thicker than the anterior end and the sclera facing surface converges towards the orbital facing surface from the posterior end to the anterior end forming a wedge shape.

5. The retinal repair device of claim 1, wherein the posterior end and the anterior end each include a rounded surface.

6. The retinal repair device of claim 1 wherein the elongated portion includes a protrusion which forms a ridge extending across at least a portion of a width of the elongated portion, transverse to the longitudinal axis of the elongated portion.

7. The retinal repair device of claim 6, wherein a length of the elongated portion from the posterior end to the anterior end is from 18 mm to 25 mm, the width of the elongated portion transverse to the length is from 6 mm to 10 mm, the protrusion extends from 4 mm to 8 mm across the width, and the protrusion is from 6 mm to 12 mm in height from the sclera facing surface to the sclera contacting surface.

8. The retinal repair device of claim 1, the first wing portion and the second wing portion each have a respective scleral facing surface which has a continuous concave curvature configured to match or approximate a convex curvature of the eye.

9. A retinal repair device for insertion into a periocular space adjacent a retinal tear in an eye, the retinal repair device comprising:
an elongated portion having a longitudinal axis, opposite first and second sides, a closed posterior end, a closed anterior end opposite the posterior end, a length between the anterior and the posterior ends, an orbital facing surface extending from the posterior end to the anterior end, and a sclera facing surface extending from the posterior end to the anterior end, opposite the orbital facing surface and configured to face a scleral surface of the eye with at least part of the sclera facing surface contacting the scleral surface; and
a wing having first and second wing portions extending out beyond the respective opposite first and second sides of the elongated portion in opposite directions transverse to the longitudinal axis of the elongated portion, the first and the second wing portions having respective outer free ends;
wherein the wing portions each have a length between the first or the second respective side of the elongated portion and the respective outer free end of the respective wing portion which is less than the length of the elongated portion; and
the first and the second wing portions have curved, concave sclera facing surfaces extending outwards from the respective first and second sides of the elongated portion to the respective outer free ends and configured to contact the scleral surface of the eye, wherein the curved, concave sclera facing surfaces are pre-formed prior to insertion of the device into the periocular space.

10. The retinal repair device of claim 9, wherein the elongated portion has a length from 18 mm to 25 mm, the elongated portion has a width from 6 mm to 10 mm, and the first and the second wing portions extend beyond the respective opposite first and second sides of the elongated portion from 4 mm to 8 mm.

11. The retinal repair device of claim 9, further comprising:
a bendable rod extending along at least part of the elongated portion between the posterior end and the anterior end and not extending beyond the opposite posterior and anterior ends of the elongated portion.

12. The retinal repair device of claim 11, wherein the bendable rod is completely embedded in the elongated portion.

13. The retinal repair device of claim 9, wherein a bendable rod is incorporated in one or more of the wing portions and the elongated portion.

14. The retinal repair device of claim 9, wherein the wing forms a cross-member.

15. The retinal repair device of claim 14, wherein the elongated portion and the cross-member are separate parts, and the cross member is adjustably mounted on the elongated portion for movement up and down the length of the elongated portion.

16. The retinal repair device of claim 15, wherein the cross-member is detachable from the elongated portion.

17. The retinal repair device of claim 14, wherein the wing has opposite first and second sides and is secured to the elongated portion at an asymmetrical position with the first side at a first distance from the anterior end and the second side at a second distance from the posterior end of the elongated portion, the first distance being different from the second distance.

* * * * *